US006699720B1

United States Patent
Lee et al.

(10) Patent No.: US 6,699,720 B1
(45) Date of Patent: Mar. 2, 2004

(54) INTERFERENCE-ELIMINATING MEMBRANES, TEST STRIPS, KITS AND METHODS FOR USE IN URIC ACID ASSAY

(75) Inventors: Tsai Yun Lee, Taipei (TW); Yi Chih Lei, Taipei (TW); Shi-Yuan Sheu, Taipei (TW); Yu Fen Tsai, Taipei (TW); Tai-Guang Wu, Taipei (TW); Hung-Hsiu Ho, Taipei (TW); Ming-Yen Kuo, Taipei (TW); Jiuan J. Liu, Taipei (TW); Tong H. Chang, Taipei (TW); Hsueh-Fang Chen, Taipei (TW); Liahng-Yirn Liu, Taipei (TW)

(73) Assignee: Development Center for Biotechnology, Taipei (TW)

( * ) Notice: Subject to any disclaimer, the term of this patent is extended or adjusted under 35 U.S.C. 154(b) by 0 days.

(21) Appl. No.: 09/579,430

(22) Filed: May 26, 2000

(51) Int. Cl.[7] .......................... G01N 21/78; G01N 33/52
(52) U.S. Cl. .......................... 436/91; 436/99; 436/174; 436/175; 422/56; 422/57; 422/61
(58) Field of Search ............................ 436/91, 99, 174, 436/175; 422/56, 57, 61

(56) References Cited

U.S. PATENT DOCUMENTS

| 3,536,448 | A |   | 10/1970 | Purushottamdas | 436/99 |
|---|---|---|---|---|---|
| 3,649,198 | A |   | 3/1972 | Rush | 436/99 |
| 4,072,627 | A | * | 2/1978 | Gindler | 436/99 |
| 4,110,079 | A |   | 8/1978 | Schaeffer et al. | 436/99 |
| 4,181,500 | A |   | 1/1980 | Cowsar et al. | 436/99 |
| 4,234,313 | A | * | 11/1980 | Faulkner | 436/99 |
| 4,303,409 | A |   | 12/1981 | Ogawa et al. | 436/99 |
| 4,348,208 | A | * | 9/1982 | Long | 436/99 |
| 4,957,872 | A | * | 9/1990 | Koever et al. | 436/175 |
| 5,212,066 | A | * | 5/1993 | Albarella et al. | 435/28 |
| 5,710,372 | A | * | 1/1998 | Becket | 73/53.01 |

FOREIGN PATENT DOCUMENTS

EP          0456098          11/1991

OTHER PUBLICATIONS

Gindler E.M. "Automated Determination of Uric Acid via Repunctive Formation of Lavender. . ." Clinical Chemistry vol. 16, No. 6 (1970) p. 536.
Pachla, L.A. et al."Analytical Methods for Measuring Uric Acid in Biological Samples and Food Products." J. Assoc. Off. Anal. Chem., vol. 70, No. 1 (1987) pp1–14.
Wu. H. "Contribution To The chemistry of Phosphomolybdic Acids. . ." Journal of Biological Chemistry, vol. XLIII, No. 1 (1920) pp 189–220.

* cited by examiner

*Primary Examiner*—Jill Warden
*Assistant Examiner*—Latoya Cross
(74) *Attorney, Agent, or Firm*—Ladas & Parry

(57) ABSTRACT

The present invention relates to an interference-eliminating membrane for use in detecting uric acid in a sample, comprising a compound for inhibiting or shading uric acid interfering substances, or derivatives thereof, and a carrier having an absorption property and permeability for the sample; and a process for preparing the interference-eliminating membrane.

The present invention also provides a test strip for use in detecting uric acid in a sample, comprising a reagent reaction layer or optional interference-eliminating membranes and/or support layers; and a kit comprising the test strip of the invention.

12 Claims, 10 Drawing Sheets

INTERFERENCE-ELIMINATING MEMBRANES, TEST STRIPS, KITS AND METHODS FOR USE IN URIC ACID ASSAY

FIELD OF THE PRESENT INVENTION

The present invention relates to an interference-eliminating membrane, test strips, kits and methods for use in detecting uric acid in a sample.

BACKGROUND OF THE INVENTION

The measurement of uric acid in blood serum or other body fluids is a very useful and valuable tool for diagnosing and monitoring the course of a variety of pathological conditions. For example, when uric acid is present at an abnormally high concentration in the blood, it tends to be crystallized in the body joints, which causes a very painful inflammatory condition, known as gout. High uric acid blood levels are also known to be associated with such conditions as uremia, which is characterized by an excessive destruction of white blood cell nuclei, e.g., leukemia and pneumonia.

There are many substances, such as ascorbic acid, in blood serum and urine, which may be mistaken for uric acid in conventional assays. If a patient is mistakenly diagnosized as having a high level of uric acid, the patient may be erroneously subjected to a dangerous, expensive, uncomfortable, and unnecessary treatment. Therefore, the accurate determination of uric acid is not easily achieved but is essential.

There are some methods, such as a chemical or enzymatic method, for the determination of uric acid. Regarding the chemical methods for use in detecting uric acid, U.S. Pat. No. 4,348,208 taught that the reduction of alkaline phosphotungstate to tungsten blue may be used. Gindle E. M., Clin. Chem 1970; 16:536 disclosed the reduction formation of deep violet chelate of Cu(I)-2,2'-bicinchoninate (BCA). However, the chemical methods would be affected by interfering substances (such as ascorbic acid) in the samples, and thus the specificity is poor. Therefore, the enzymatic methods for detecting uric acid were gradually replaced between 1980–1990.

The enzymatic methods are characterized by the measurement of the absorbance of uric acid at a wavelength ranging from 290 to 293 nm. No absorbance of the reaction products of uricase will be detected at this wavelength. The absorbance decrease of uric acid after incubation with uricase is proportional to the initial value. Although the specificity of the enzymatic methods is relatively high, persons who conduct the detection of uric acid always have to pay more attention to maintain stability. In addition, enzymatic methods are more expensive than chemical methods. It is not convenient to store uricase as a protein. Therefore, enzymatic methods still practiced in specific places, such as hospitals or laboratories, and cannot be applied in counters or dispensaries.

U.S. Pat. No. 4,348,208 discloses that compounds containing mercapto arc added into the mixture of an alkaline phosphotungstate reagent and a sample to detect uric acid in the sample. However, the assay protocol disclosed in the patent still requires reagent preparation and mixture before the assay begins. This method is not convenient for common users.

Although it is known that phosphotungstate in an alkaline solvent can detect uric acid, the phosphotungstate, together with base, produces an acid-basic neutralization. In addition, phosphotungstate may change to specific forms of the phosphotungstate under different conditions, which cannot be used in the detection of uric acid.

Persons skilled in the art understand that a dry chemistry method, such as test strip is more convenient in performing an assay than a wet chemistry method. Furthermore a dry chemistry method is cheaper than an enzymatic method.

There is a need in the art for uric acid test strips and/or kits having high specificity and stability to conveniently detect uric acid in over the counter pharmacies or dispensaries, and allow non-professional persons, such as patients to determine uric acid levels according to the color change of the test reagent with uric acid in a sample.

SUMMARY OF THE INVENTION

It is an object of the present invention to provide an interference-eliminating membrane for use in detecting uric acid in a sample.

It is also an object of the present invention to provide a test strip for use in detecting uric acid in a sample.

It is a further object of the present invention to provide a kit for use in detecting uric acid in a sample.

Another object of the present invention is to provide a process for use in detecting uric acid in a sample.

LEGENDS

Figure 1:
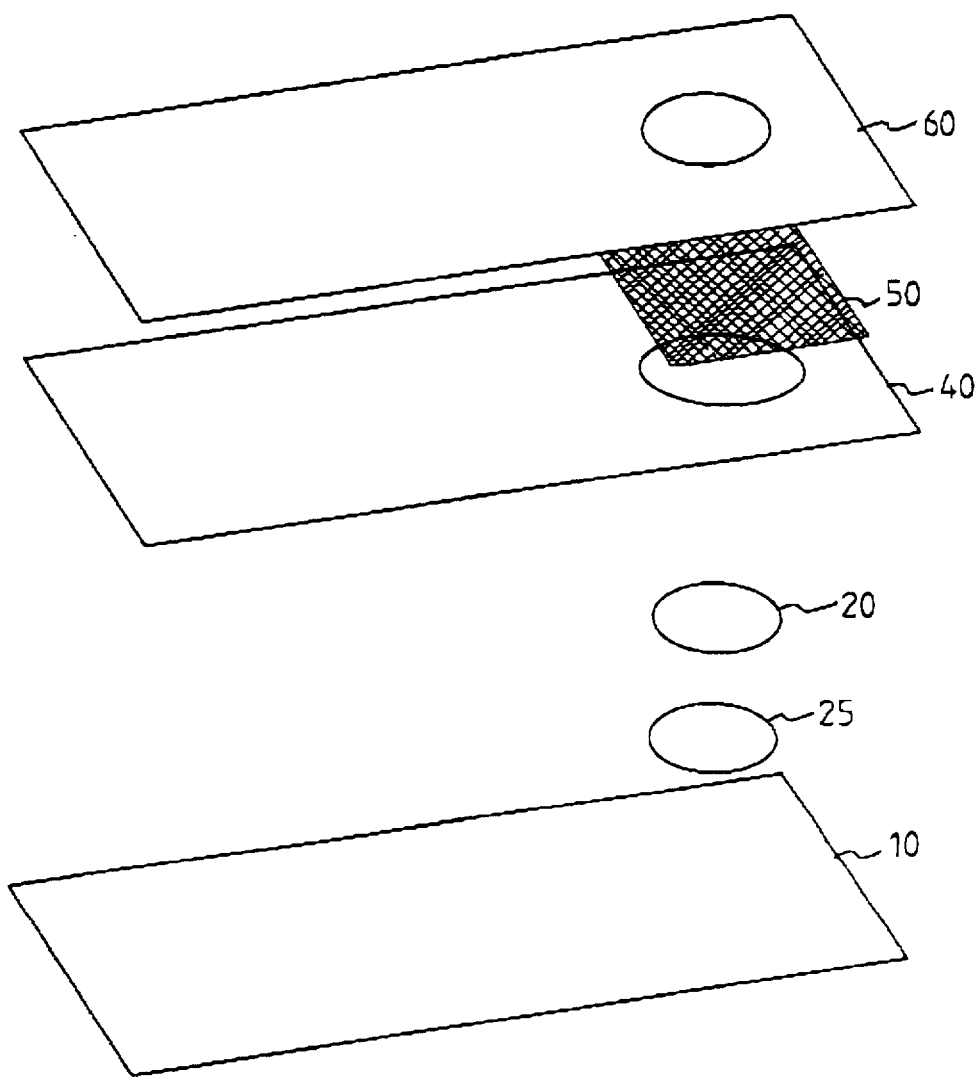
FIG. 1 represents a test strip without an interference-eliminating membrane.
Figure 2:
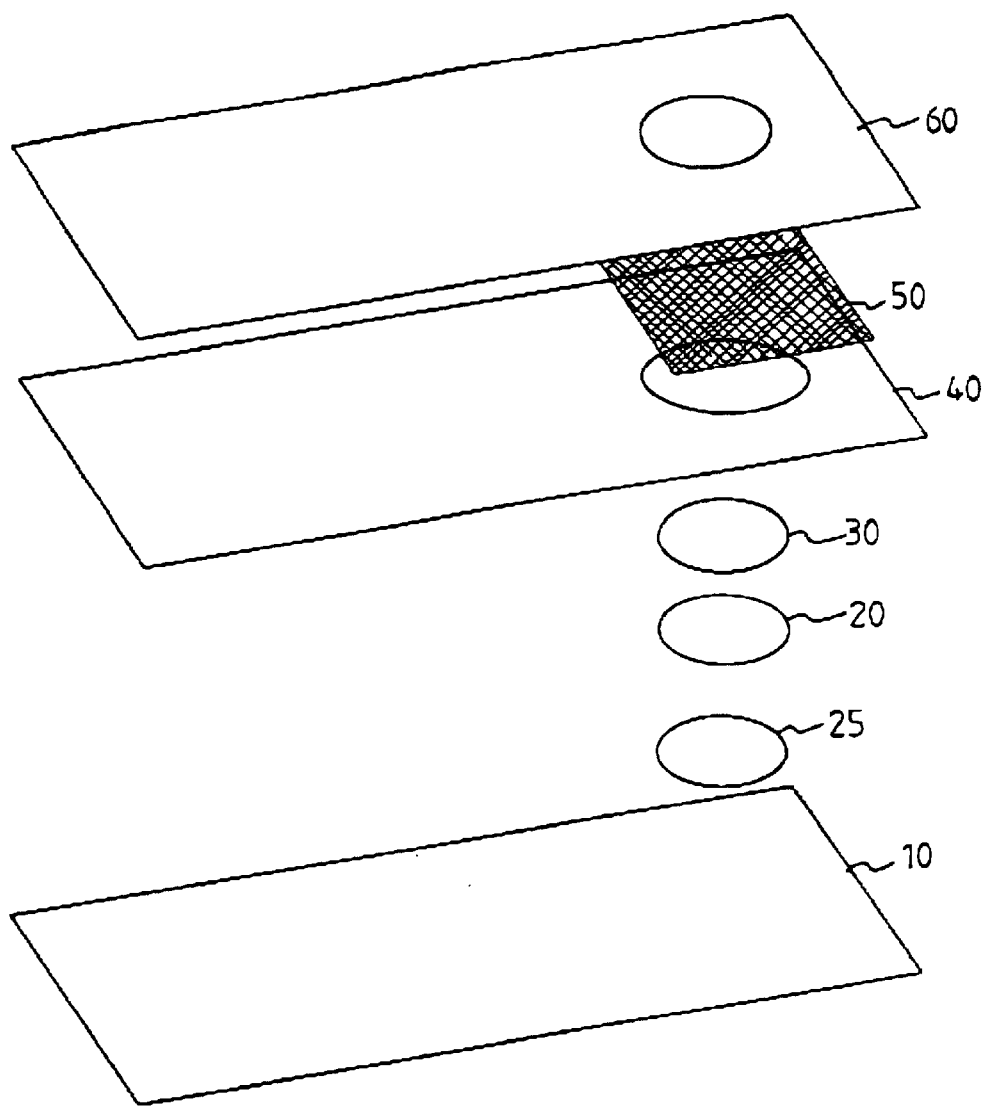
FIG. 2 represents a test strip with an interference-eliminating membrane.

The meanings of each symbol in FIGS. 1 and 2 are as follows:
10 represents a support layer.
20 represents a reagent reaction layer.
25 represents a reagent reaction layer.
30 represents an interference-eliminating membrane.
40 represents a plastic plate.
50 represents a net membrane.
60 represents a plastic plate.

DETAILED DESCRIPTION OF THE INVENTION

The present invention firstly provides an interference-eliminating membrane for use in detecting uric acid in a sample. It comprises a compound for inhibiting or shading uric acid interfering substances, or derivatives thereof, and a carrier having an absorption property and permeability of the sample wherein said compounds can selectively oxidize a substance having a reducing ability higher than that of uric acid in a sample or carry one or more mercapto groups to shade a substance interfering uric acid assay in a sample.

The term "a compound for inhibiting uric acid interfering substances or derivatives thereof", as used herein refers to the compounds useful in inhibiting uric acid interfering substances or derivatives thereof. In particular, the compounds, or derivatives thereof, can quickly oxidize a substance having a reducing ability higher than that of uric acid, such as ascorbic acid, under a specific pH (preferably less than 5, most preferably less than 1). The preferred embodiments are selected from the group consisting of iodate, ferrate, $KMnO_4$, $K_2Cr_2O_7$, $K_2CrO_4$ and $Ce(SO_4)_2$. The most preferred embodiment is potassium iodate.

The term "a compound for shading uric acid interfering substances or derivatives thereof", as used herein refers to the compounds useful in shading uric acid interfering substances or derivatives thereof The compound carries one or more mercapto groups, which are preferably selected from the group consisting of cysteine and glutathion. The most preferred embodiment is cysteine. The compounds are not essential components of the active ingredient in the test strips of the invention, but enhance the specificity of uric acid assay. To date, compounds containing mercapto group have not been used in the uric acid assay based on $Cu^{2-}$ ion and bicinchoninate.

The term "a carrier having an absorption property and permeability of the sample," as used herein, refers to a material which loads a sample and allows the sample to flow into the reagent reaction layer for reaction. The material is preferably selected from a group consisting of nonwoven fabrics, filter paper, nitrocellulose membranes, nylon membranes or glass fibers. Nonwoven fabrics are the most preferable. The color of the carrier is not specified but cannot affect the color resulted from the reaction of the reagents with samples. The color of the carrier is preferably a light one or white, most preferably white.

It has been reported that the reaction between phosphotungstic acid with a basic material forms an acid-basic neutralization and the reaction between $Cu^{2-}$ ion and bicinchoninate produces precipitation. In addition, phosphotungstate under different conditions may change to specific forms of phosphotungstate, which cannot be used for in the detection of uric acid. Therefore, in general diagnostic analysis, operators have to add phosphotungstic acid, the specimen and base in a correct order and correct volumes. Given the above, if the above disadvantages cannot be removed, it is impossible to develop a test strip containing the reagents for use in a uric acid assay. Surprisingly, if the reagents do not have substantive reactions each other before the addition of a sample, the disadvantages of The reagents can be removed. More specifically, the reagents can be coated with different positions or surfaces in the same reaction layer or different reaction layers to avoid causing the the neutralization and precipitation of the reagents. The users only have to apply samples into the test strip to easily accomplish uric acid assay.

Accordingly, the present invention further provides a test strip for use in detecting uric acid in a sample, comprising one or more reaction layers, including test reagents and a carrier, wherein the test reagents are selected from a group consisting of (a) phosphotungstic acid, salts or derivatives thereof, and basic materials, provided that the phosphotungstic acid, salts or derivatives thereof cannot have a substantive reaction with the basic material before the addition of the sample, or (b) a $Cu^{2+}$ ion and bicinchoninate, provided that the $Cu^{2+}$ ion cannot have a substantive reaction with bicinchoninate before the addition of the sample.

The source of the $Cu^{2+}$ ion may be obtained from a compound providing $Cu^{2+}$ ion or derivatives thereof, which is preferably obtained from copper sulfate. One of the preferred embodiments for bicinchoninate is sodium bicinchoninate. Since the precipitation from the reaction between the $Cu^{2+}$ ion and bicinchoninate during mixing may occur, such precipitation makes the preparation of reaction layers troublesome. To avoid causing precipitation, citrate (such as sodium citrate) may be added during the mixing of the $Cu^{2-}$ ion with bicinchoninate.

The term "reaction layer," as used herein, refers to a carrier which loads the reagents and can be selected from a group of nonwoven fabrics, filter paper, glass fibers, nitrocellulose membranes or nylon membranes.

Further, some samples (such as saliva) have little or no uric acid interfering substances. However, there are a few samples, such as blood, having a reducing ability higher than that of uric acid, such as ascorbic acid, to interfere in a uric acid assay. The test strip of the invention may further comprise the interference-eliminating membrane of the invention. The membrane situates above the reagent reaction layers or incorporates itself into the reagent reaction layers or positions between the different test reagent layers. In the membrane, a compound for inhibiting uric acid interfering substances or derivatives thereof does not affect the reaction of the test reagents with uric acid.

The phosphotungstic acid reagent, as used herein, may be of a grade for use in a clinical laboratory. Before synthesis, the reagents were added with excess phosphoric acid. The reagent can be directly used in the uric acid assay without the purifying or processing of phosphotungstic acid to become such as a salt. However, if the phosphotungstic acid reagent is directly used in the preparation of the test strip for a uric acid assay, sodium carbonate and excess phosphoric acid result in a neutralization reaction, and thus produce a $CO_2$ bubble, which cannot thoroughly or slowly allow further sample fluids to permeate into the position in situ. Surprisingly, the synthesized phosphotungstic acid solution can be modified to an appropriate pH value, such as pH 2–5, to reduce the difference between the test strips and elevate the reaction rate of the reagent.

According to the invention, the use of ammonium phosphotungstate salts in a uric acid assay can significantly improve the effects of the test strips without purification or pH modification. The ammonium salts without pH modification can be directly used in a uric acid assay to reduce the standard deviations in assays and exclude the excess buffer effects obtained from the other salts.

Accordingly, phosphotungstic acid, salts or derivatives thereof. used in the test snips of the invention are preferably at pH 2–5, mole preferably 3.8. The preferred embodiment of the phosphotungstates is ammonium phosphotungstate.

A basic material used in the test strips of the invention refers to a compound or its derivatives providing a base. The basic material is preferably selected from a group consisting of carbonate. glycine, carbonate-ureidoethanolamine or sodium hydroxide. The most preferred basic material is carbonate.

The carriers used in the test strips of the invention consist of a substance for absorbing fluid. The substance is preferably selected from a group consisting of nonwoven fabrics, filter paper, nitrocellulose membranes, nylon membrances or glass fibers. The most preferred carrier is filter paper.

The test strips of the invention further comprise a support (such as plastic plate) and/or a net membrane which are located at the top of the test strips. The net membrane can uniformly diffuse the sample to facilitate the assay. The support is used in supporting carriers and/or the net membrane.

The samples used for the test strips of the invention include, but does not limit, blood, serum, saliva or urine. If the sample is saliva or urine, the assay for uric acid detection can be conveniently conducted in over the counter pharmacies or dispensaries.

The invention further provides a kit for use in detecting uric acid in a sample, comprising the test strips of the invention. The kit further comprises a color card or a handy photometer comparing the test results for the determination of the assay results.

The sample used for the kits includes, but does not limit, blood, serum, saliva or urine. If the sample is saliva or urine, the assay for uric acid detection can be conveniently conducted in over the counter pharmacies or dispensaries.

As the different concentrations of uric acid in a sample affect the color change of the reagent from almost white to deep blue or violet, the assay results can be compared with the color card or a handy photometer to facilitate quantitative and qualitative analysis. The color development may be stored as digital or analog data under the reaction of different uric acid concentrations with reagents.

The invention further provides a method for use in detecting uric acid in a sample, comprising the steps as follows:

(a) using the interference-eliminating membrane of the invention to inhibit interference due to uric acid interfering substances in the sample;

(b) reacting the reagents for the uric acid assay with the sample of step (a) without interfering substances; and (c) observing the color change of the reagent.

The reagents for the uric acid assay in step (b) are phosphotungstic acid, salts or derivatives, and a base material. The phosphotungstic acid or its derivatives are preferably pH 2–5, most preferably 3.8. The most preferred phosphotungstate is ammonium phosphotungstate. A basic material used in the test strips of the invention refers to a compound or its derivatives providing basic property. The basic material is preferably selected from a group consisting of carbonate, glycine, carbonate-ureidoethanolamine or sodium hydroxide. The most preferred basic material is carbonate.

The color change of the reagent in step (c) is from almost white to deep blue or violet, under different concentrations of uric acid.

The sample used for the methods of the invention includes, but does not limit, blood, serum, saliva or urine. If the sample is saliva or urine, the assay for uric acid detection can be conveniently conducted in over the counter pharmacies or dispensaries.

The assay results can be determined by a handy photometer or conveniently compared with the color card in the kits to facilitate quanititative and qualitative analysis. Therefore, the method of the invention further comprises a step of colorimetric analysis to compare the resulting color of the reagents with a color card. The resulting data is corepared with the photometric data of the reagents under different uric acid concentrations.

To facilitate the further understanding of purpose, methods, characteristics and principles of the invention, the following examples illustrate various aspects of the present invention, but do not limit the claims in any manner whatsoever.

EXAMPLES

Example 1

The Preparation of the Test Strips

1. The Preparation of the Solution of Ammonium Phosphotungstate

To a solution of $Na_2WO_4 \cdot 2H_2O$ (200 g) in water (1L) was added 85% phosphoric acid (280 g). The mixture was heated for 8 hours at its boiling point under return condenser. When the heating period was almost completed, the solution was concentrated to about a 1 L volume. A few drops of bromine water was added to the solution to change the color of the solution to pure yellow. If no further treatment should be made, the solution was a reagent of phosphotungstic acid, for use in a clinical assay. After cooling, the solution was admixed with powder, $NH_4Cl$ (200 g). The crystalline precipitate was sucked and filtered, and then was re-dissolved in water and re-precipitated with solid $NH_4Cl$. The step was repeated twice. After this, the resulting precipitate was dissolved in about 600 c.c. water.

2. The Preparation of Test Strip of Phosphotungstic Acid

The filter paper containing cellulose, such as Toyo 7 filter paper, was immersed in a solution of ammonium phosphotungstate overnight. Then, the filter paper was removed from the solution, dripped dry of excess liquid and dried at 55° C. in aoven.

3. The Preparation of Test Strip of Sodium Carbonate

The nonwoven fabrics were immersed in a solution of 25% sodium carbonate overnight. Then, the filter paper was removed from the solution, dripped dry of excess liquid and dried at 55° C. in an oven.

4. The test strips of phosphotungstic acid and sodium carbonate were respectively cut into a round disk, 5 mm in diameter. The former was represented as membrane A and the latter was represented as membrane B. Alternatively, the former was represented as membrane B and the latter was represented as membrane A. Then, membrane A was adhered to membrane B to form a reaction layer.

5. The Preparation of Interference-eliminating Membrane

Nylon membrane of 150 mesh was immersed in a solution of $KIO_3$ (1000 mg/dl) in water for 60 minutes. Then, the filter paper was removed from the solution, dripped dry of excess water and dried at 55° C. in an oven overnight to form an interference-eliminating membrane. Tile membrane was cut into a round disk, 5 mm in diameter.

6. The Construction of the Test Strip

As illustrated in FIG. 1, a transparent support layer (10) was adhered to membrane A (25) and membrane B (20). The plastic plates (40, 60) have a round hole of 0.5 cm in diameter. The hole of the plate (40) was firstly positioned above membrane B and adhered to the membrane. Then, the net membrane (50) and the other plate (60) were sequentially adhered to the plate (40) to form a test strip without an interference-eliminating membrane.

As illustrated in FIG. 2, a transparent support layer (10) was adhered to the round shaped membrane A (25) and membrane B (20). Then, the interference-eliminating membrane (30). 5 mm in diameter, was adhered to the membrane B. The plastic plates (40, 60) have a round hole of 0.5 cm in diameter. The hole of the plate (40) was first positioned above the interference-eliminating membrane (30) and adhered to the membrane. Then, the net membrane (50) and the other plate (60) were sequentially adhered to the plate (40) to form a test strip with an interference-eliminating membrane.

Example 2

The Effects on the Absorbance of Ascorbic Acid With or Without Iodate

Figure 3A:
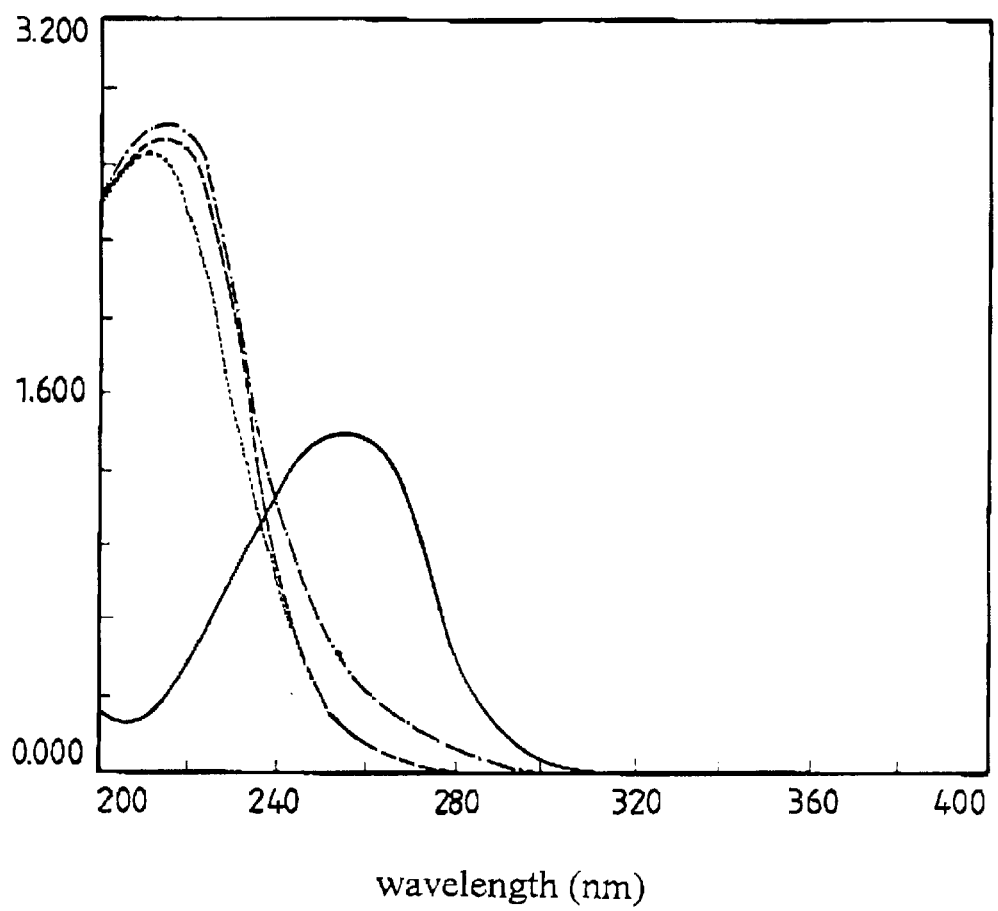
FIG. 3 represents (a) the spectra of reacting ascorbic acid with potassium iodate under $1.0 \times 10^{-4}$ N hydrochloric acid, (b) the spectra of reacting ascorbic acid with potassium iodate under $1.0 \times 10^{-5}$ N hydrochloric acid, and (c) the spectra of mixing uric acid and potassium iodate. In (a), —• represents the curve after mixing ascorbic acid with potassium iodate for 0 second. —— represents the curve after mixing ascorbic acid with potassium iodate for 45 seconds (in the mixture, the concentration of ascorbic acid is 3 mg/dL, the ratio of potassium iodate is 0.035% and the concentration of HCl is $1.0 \times 10^{-4}$N). — represents the curve of 3mg/dL ascorbic acid. ••••• represents the curve of 0.035% potassium iodate containing $1.0 \times 10^{-4}$N HCl. In (b), —, —— and —• represent the curves after mixing ascorbic acid with potassium iodate for 0, 2 and 10 minutes, respectively. —•• represents the curve after mixing ascorbic acid with potassium iodate for 30 minutes (in the mixture, the concentration of ascorbic acid is 3 mg/dL, the ratio of potassium iodate is 0.035% and the concentration of HCl is $1.0 \times 10^{-5}$N). — represents the curve of 3 mg/dL ascorbic acid. ••••• represents the curve of 0.0035% potassium iodate containing $1.0 \times 10^{-5}$N HCl. In (c), —•— represents the curve after ascorbic acid with potassium iodate for 0 second (the spectra does not change within 7 minutes) (in the mixture, the concentration of ascorbic acid is 3 mg/dL, the ratio of potassium iodate is 0.035% and the concentration of HCl is $1.0 \times 10^{-4}$N). — represents the curve of 3 mg/dL uric acid. ••••• represents the curve of 0. 035% potassium iodate containing $1.0 \times 10^{-4}$N HCl.
Figure 3B:
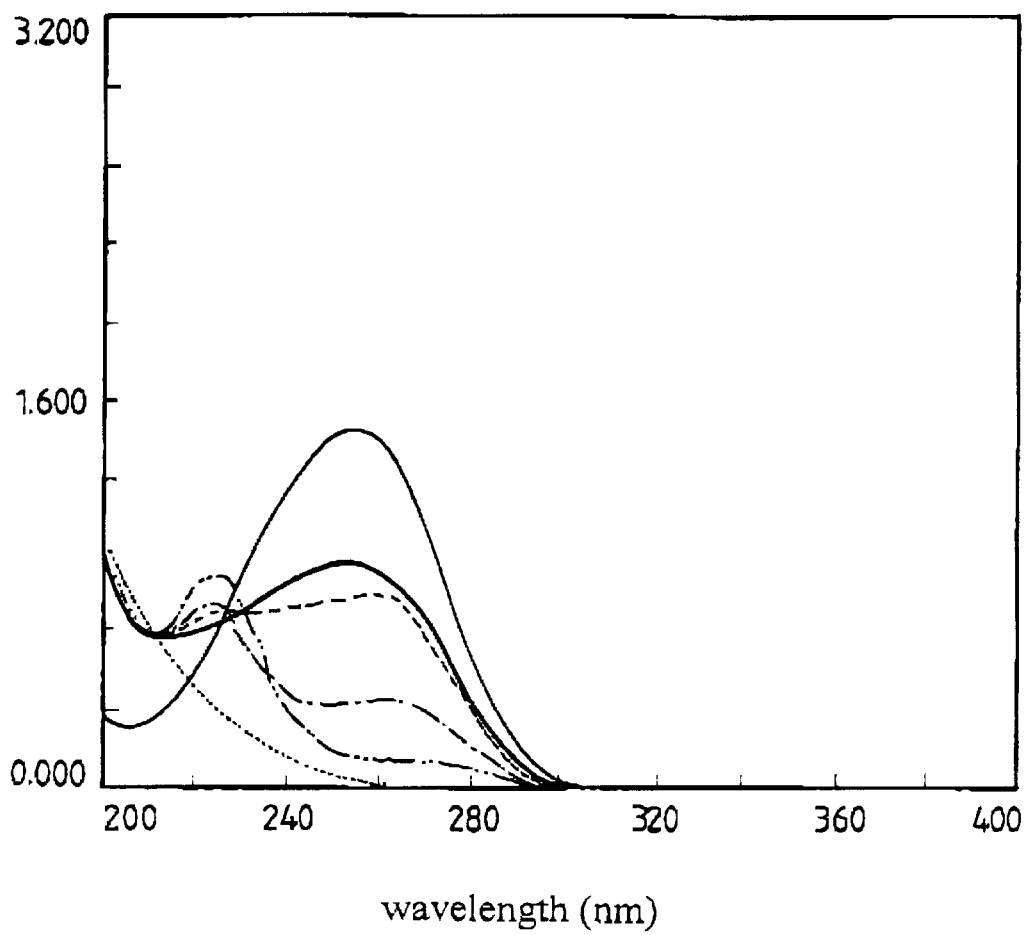
Figure 3C:
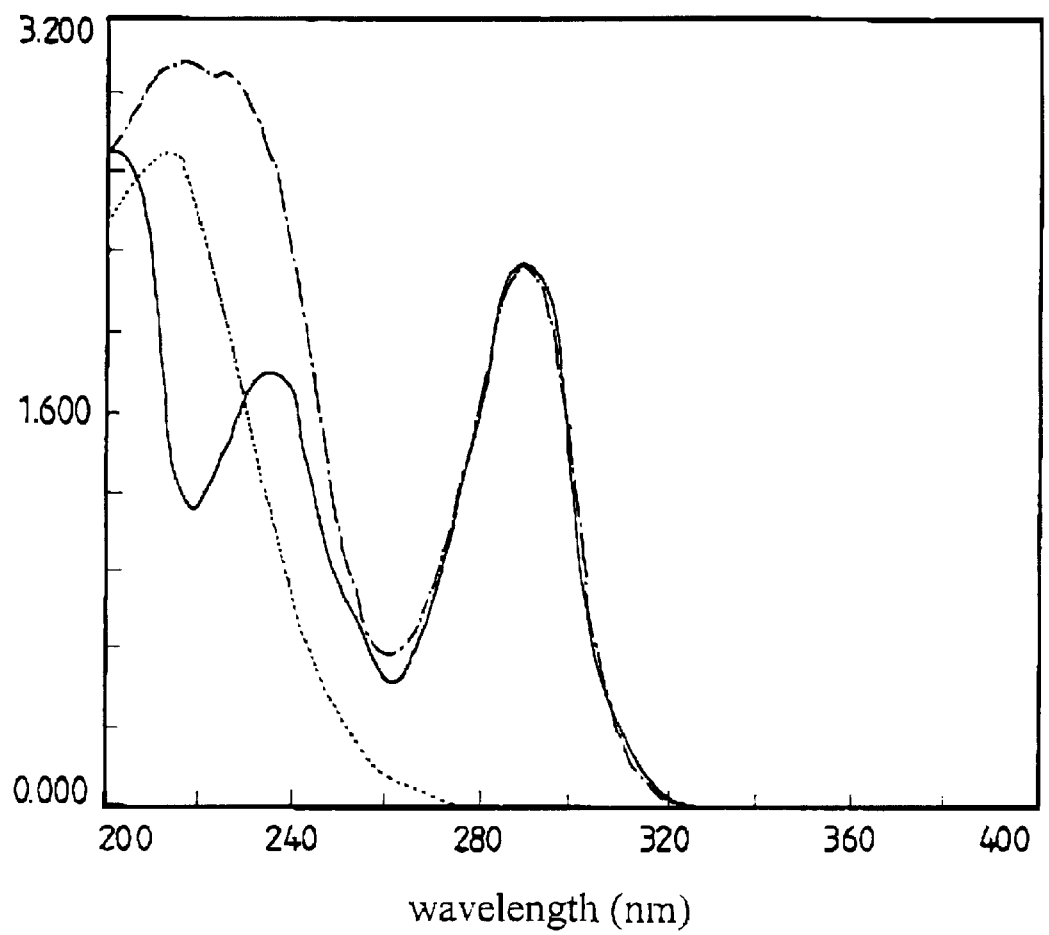

In different cuvettes, to 30 μl ascorbic acid standard solution, an iodate solution of 10 mg/dl under a different quantity of hydrochloric acid was added dropwise. The absorbance of the solution was determined by a spectrophotometer (Becham DU-70). The results are shown in FIG. 3. The absorbance peak of ascorbic acid around 260 nm was flattened by the addition of iodate. The higher the concentration of hydrochloric acid was present in the iodate solution, the quicker the reaction between ascorbate and iodate was occurred. The lower the concentration of hydrochloric acid was present in the solution, the slower the reaction progressed (FIG. 3b). However, iodate, in the same tests, did not inhibit the absorbance of uric acid (FIG. 3c). In particular, FIG. 3a represented the spectra of reacting ascorbic acid with potassium iodate under $1.0 \times 10^{-4}$ N hydrochloric acid. After mixing, ascorbic acid was quickly oxidized by potassium iodate. The absorption peak disappeared within one minute. FIG. 3b represented the spectra of reacting ascorbic acid with potassium iodate under $1.0 \times 10^{-5}$ N hydrochloric acid. After mixing, ascorbic acid was gradually oxidized by potassium iodate. FIG. 3c represented the spectra of mixing uric acid with potassium iodate. After mixing, the absorption characteristics almost completely maintained within 7 minutes and was consistent with the original spectra of uric acid. It indicated that uric acid was not oxidized by potassium iodate.

Example 3

The Effects on the Uric Acid Assay With or Without an Interference-eliminating Membrane (IEM)

In IEM containing $KIO_3$, the effect of $NaHSO_4$ concentrations on the test results

| Samples applied the test strips | L value | Without IEM | $NaHSO_4$ concentrations | | | | |
|---|---|---|---|---|---|---|---|
| | | | 0.001M | 0.01M | 0.1M | 0.3M | 1M |
| Blank solution* | | 74.18 | 72.52 | 73.03 | 73.61 | 72.80 | 73.34 |
| 10 mg/dl uric acid | | 60.25 | 60.71 | 60.34 | 60.46 | 58.87 | 64.07 |
| 10 mg/dl ascorbic acid | | 57.53 | 60.51 | 62.71 | 66.39 | 71.39 | 71.48 |

* the blank solution was a 20 mM PBS buffer solution and $KIO_3$ concentrations in IEM was 0.2%.

In the above table, the test strips with IEM containing $NaHSO_4$, with concentrations higher than 0.3M, did not show a significant blue color 2 minutes after the addition of ascorbic acid and their L values were close to those of the blank solution. To the contrary, the test strips without IEM or with the IEM containing $NaHSO_4$, less than 0.1M, showed significant blue color 2 minutes after the addition of ascorbic acid and their L values were not higher than 66.39. On the other hand, if the test strips comprised IEM and the pH value of the material therein was modified to appropriate levels, the interference of ascorbic acid could be inhibited within two minutes after the sample was added. Further, the example demonstrated that the IEM did not significantly affect the uric acid assay, except that the strips a light blue color under 1M NaHSO$_4$.

Example 4

The Effects on Phosphotungstic Acid (PTA) Due to pH Values

Figure 4:
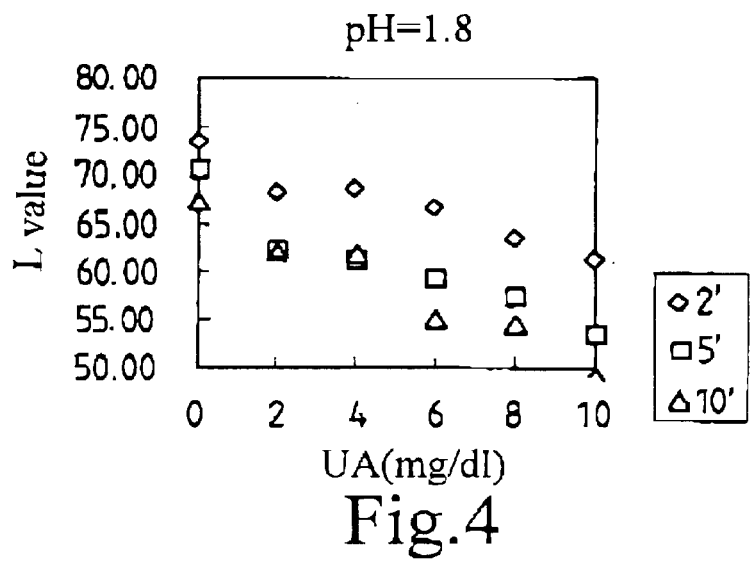
FIG. 4 represents the determination results on the reaction of untreated clinical phosphotungstic acid with uric acid. In the figure, the vertical axis represents a brightness, L value, of the test reaction layer determined by a reflectmeter, and the horizontal axis represents uric acid levels in the same sample, determined by enzymatically quantitative analysis.

1. Six test strips using untreated PTA were applied to a uric acid standard solution (10 mg/dl). As illustrated in FIG. 4, the standard derivation at 2' was up to 4.51 (L value). The PTA was untreated under ph 1.8. The data was shown as follows

| Stability of color development: 10 mg/dl UA | | | |
|---|---|---|---|
| strip # | 2' | 5' | 10' |
| 1 | 62.86 | 58.17 | 55.24 |
| 2 | 65.12 | 64.39 | 61.31 |
| 3 | 64.66 | 57.65 | 52.24 |
| 4 | 63.50 | 56.54 | 52.62 |
| 5 | 57.39 | 55.46 | 52.92 |
| 6 | 71.41 | 68.30 | 66.24 |
| Average | 64.16 | 60.09 | 56.76 |
| SD | 4.51 | 5.09 | 5.75 |
| Linearship: UA(mg/dl) | | | |
| 0 | 73.44 | 70.45 | 67.41 |
| 2 | 68.37 | 62.36 | 62.29 |
| 4 | 68.65 | 61.14 | 61.89 |
| 6 | 66.64 | 59.13 | 55.13 |
| 8 | 63.49 | 57.21 | 54.53 |
| 10 | 61.07 | 53.20 | 49.21 |
| $R^2$ | 0.9398 | 0.9101 | 0.9574 | in addition, the linear relationship along with duration, after the addition of the sample, will be different. That is, the longer the reaction time of the sample was applied to the test strip, the deeper the color of the reagent showed.

Figure 5:
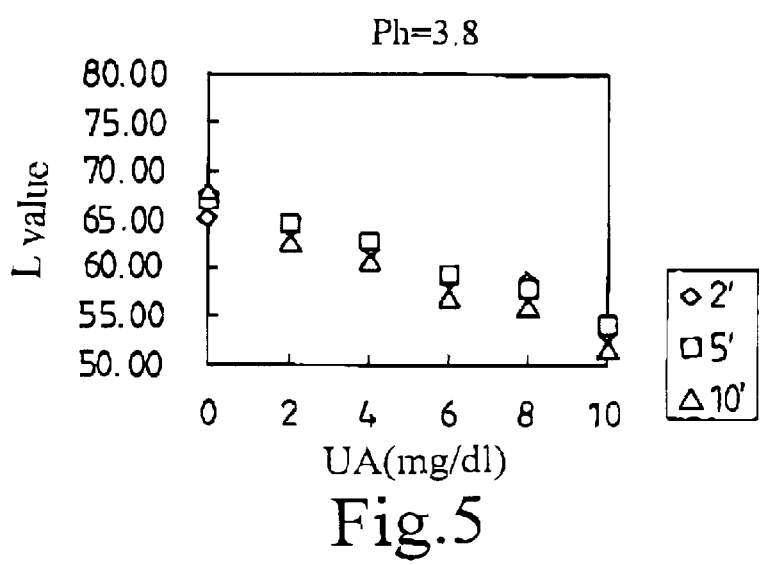
FIG. 5 represents the determination results using the test strips based on the reaction of uric acid with a phosphotungstic acid reagent of which the pH value was modified to 3.8 by 1N NaOH. In the figure, the meanings of the vertical and horizontal axes are the same as FIG. 4.

2. Six test strips, wherein the pH of PTA was modified to 3.8 by the treatment of 1N NaOH, were applied to a uric acid standard solution (10 mg/dl). As illustrated in FIG. 5, the standard derivation was lowered to 0.79. The pH of PTA was adjusted to 3.8. The data was shown as follows:

| Stability of color development: 10 mg/dl UA | | | |
|---|---|---|---|
| strip # | 2' | 5' | 10' |
| 1 | 54.22 | 54.02 | 50.76 |
| 2 | 55.74 | 55.28 | 54.28 |
| 3 | 56.14 | 54.93 | 53.59 |
| 4 | 55.20 | 54.79 | 52.52 |
| 5 | 55.17 | 53.17 | 50.60 |
| 6 | 54.20 | 53.91 | 52.76 |
| Average | 55.11 | 54.35 | 52.42 |
| SD | 0.79 | 0.79 | 1.48 |
| Linearship: UA(mg/dl) | | | |
| 0 | 65.20 | 67.05 | 68.06 |
| 2 | 63.99 | 64.60 | 62.65 |
| 4 | 62.21 | 62.64 | 60.71 |
| 6 | 58.82 | 59.17 | 56.83 |
| 8 | 58.28 | 57.64 | 55.89 |
| 10 | 53.58 | 53.74 | 51.78 |
| $R^2$ | 0.9527 | 0.9888 | 0.9693 |

Further, the reaction between the reagent and the analyte at 2' was almost completed. The test data at 2' was almost the same as those at 10'. Given the above, the pH modification reduced the difference between the test strips and increased the reaction rate of the test strips.

Example 5

The Effects on the Solution of PTA Due to Ammonium Salt Formation

Figure 6:
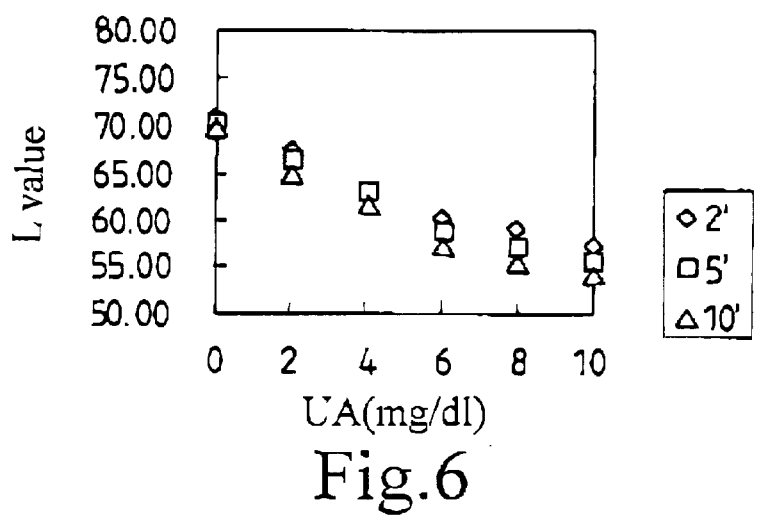
FIG. 6 represents the determination results using the test strips on the reaction of uric acid with an ammonium phosphotungstate reagent. In the figure, the meanings of the vertical and horizontal axes are the same as FIG. 4.

The solution of PTA ammonium salt, as prepared according to Example 1 for use in uric acid assay significantly improved the effects of the test strips without the need for purification or pH modification. The PTA ammonium salts needed no pH modifications and could be directly used in an assay. As illustrated in FIG. 6, the standard derivation at 2' was lowered to 0.86. The data was shown as follows

| Stability of color development: 10 mg/dl UA | | | |
|---|---|---|---|
| strip # | 2' | 5' | 10' |
| 1 | 57.26 | 56.56 | 54.51 |
| 2 | 55.82 | 55.45 | 56.10 |
| 3 | 57.41 | 56.77 | 55.97 |
| 4 | 58.05 | 57.23 | 54.29 |
| 5 | 57.96 | 57.85 | 56.50 |
| 6 | 58.06 | 57.59 | 56.43 |
| Average | 57.43 | 56.91 | 55.63 |
| SD | 0.86 | 0.86 | 0.98 |
| Linearship: UA(mg/dl) | | | |
| 0 | 70.68 | 70.46 | 69.85 |
| 2 | 67.50 | 66.28 | 64.98 |
| 4 | 63.58 | 63.19 | 61.90 |
| 6 | 60.17 | 58.85 | 57.24 |
| 8 | 59.14 | 57.04 | 55.54 |
| 10 | 57.03 | 55.44 | 54.18 |
| $R^2$ | 0.9680 | 0.9720 | 0.9595 |

In addition, the blue color was not significantly deepened along with extension of reaction time. Given the above, the preparation of PTA ammonium salt with higher purity did not require complex procedures. In addition, PTA ammonium salt removed excess buffering effects obtained from other salts.

The synthesis of PTA reagent used in the clinical assay was the same as that of PTA ammonium salt. However, the former did not add ammonium chloride to conduct precipitates for separation. Therefore, the former included higher concentrations of phosphoric acid and the untreated PTA. As the compounds other than PTA were relatively high in concentration resulting in buffer effects, the rate of sodium carbonate neutralizing PTA tended to be slow and further reduced the reaction of PTA and uric acid.

Example 6

The Determination on Quantity of the Sample to be Tested

1. The Determination on Quantity of Uric Acid in Saliva

Figure 7A:
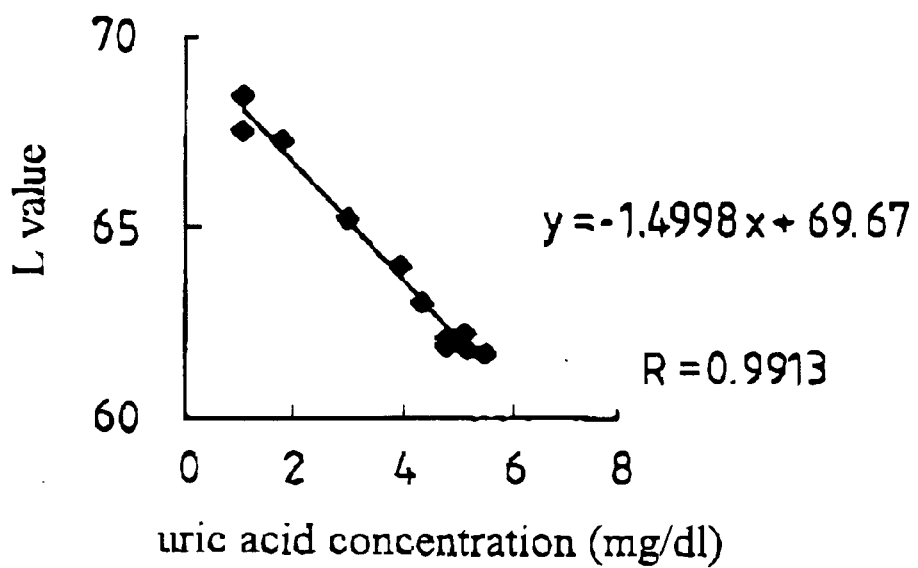
FIG. 7 represents the determination results using the test strips on uric acid in (a) saliva and (b) serum. In the figure, the meanings of the vertical and horizontal axes are the same as FIG. 4.

Saliva was randomly collected from 11 individuals, and 20 μl saliva per person was added to the PTA test strips. After two minutes, the brightness of the color appearing on the reagent layer of test strips was determined with a reflector. The results were illustrated in FIG. 7a. The vertical axis represented a brightness L value of the reagent reaction layer determined by a reflector, and the horizontal axis represented uric acid levels in the same sample determined by enzymatically quantitative analysis. L value of each sample was the average of the reflectness showed on three test strips.

2. The Determination on Quantity of Uric Acid in Serum

Figure 7B:
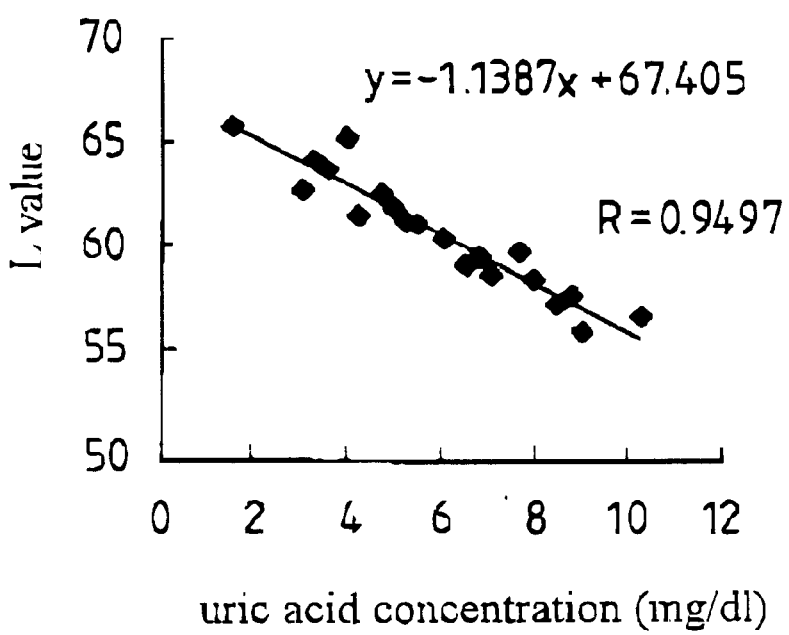

The determination method was the same as that of the quantity of uric acid in saliva, except that the samples were replaced with 20 sera. The results were showed in FIG. 7b.

Example 7

The Effects on the Absorbance of Ascorbic Acid With or Without Cysteine

The solution containing 0.08%(w/v) copper sulfate and 0.02M sodium citrate was prepared. After stirring the solution. 1.28%(w/v) sodium bicinchoninate was added to the solution to form a mixture. Then, filter paper was immersed in the mixture. The immersed paper was dried and cut to produce a test reagent reaction layer. The nonwoven fabrics were immersed in the solution of 2 g/dl cysteine in $NaH_2PO_4$. The immersed fabrics were dried and cut to produce an interference-eliminating membrane. The test strip was constructed according to the similar method of Example 1.

20 μl urine was added to the test strip After 20 seconds, a violet color appeared on test strips if uric acid was present in the sample. The test results were determined with a reflectmeter (Nippon, NR-3000) at a wave length of 557 nm or were compared with a color card in in the kit.

The test groups were divided to (a) standard solutions of cysteine, uric acid and ascorbic acid, respectively, (b) uric acid standards containing 0, 2 and 10 mg/dl ascorbic acid, respectively, and (C) uric acid standards containing 0, 15 and 150 mg/dl cysteine, respectively. The tests were accomplished by a photometric method. The deeper the color developed, the smaller the reflection value (Y value) obtained.

Figure 8A:
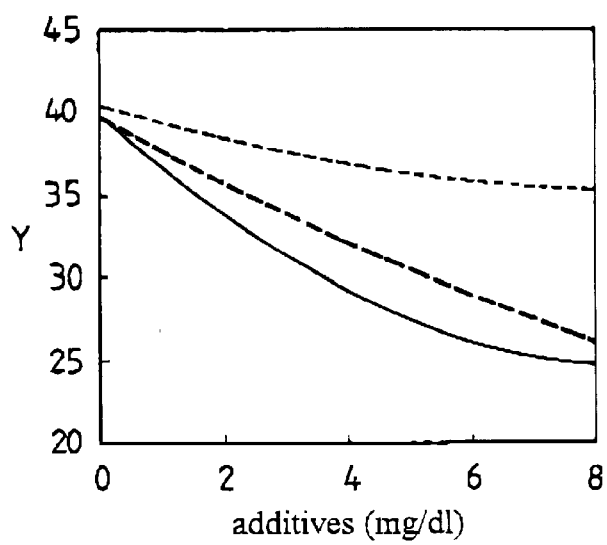
FIG. 8 represents the uric acid determination results using the test strips without an interference-eliminating membrane in the presence of ascorbic acid (AA) and cysteine, where' the vertical axis represents a reflection value at a wave length of 557 nm, Y value, and the horizontal axis represents the concentration of additives or uric acid. In (a), the lines ———, ——— and ——— respectively represent the calibration curves of cysteine, uric acid and ascorbic acid. In (b) the lines, ———, — and ••• respectively represent the calibration curves of uric acid containing 0, 2 and 10 mg/dl ascorbic acid. In (c) the lines, ———, — and ••• respectively represent the calibration curves of uric acid containing 0, 15 and 150 mg/dl cysteine.
Figure 8B:
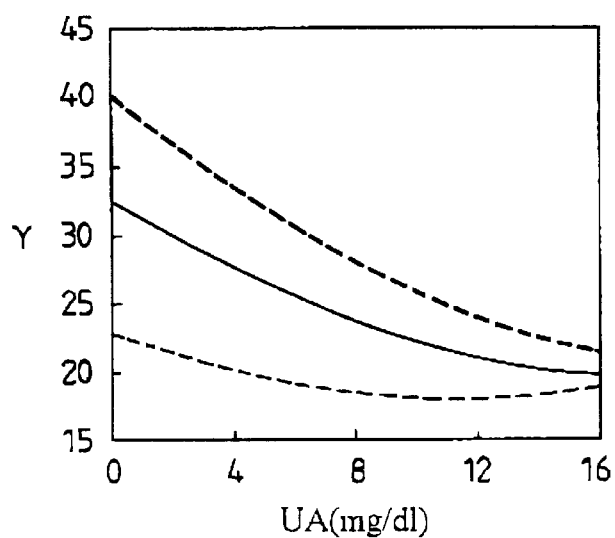
Figure 8C:
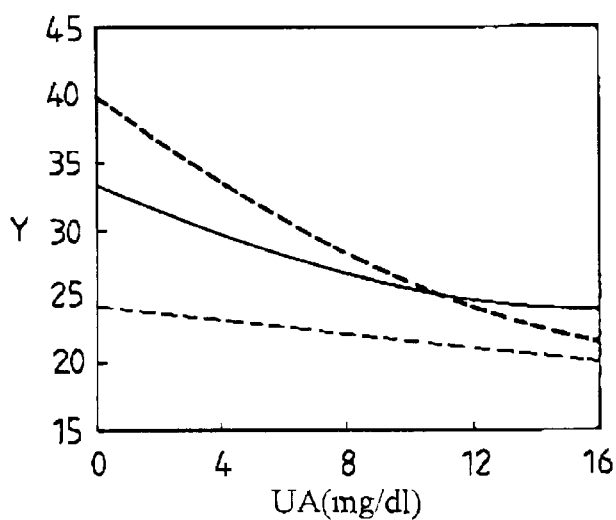
Figure 9A:
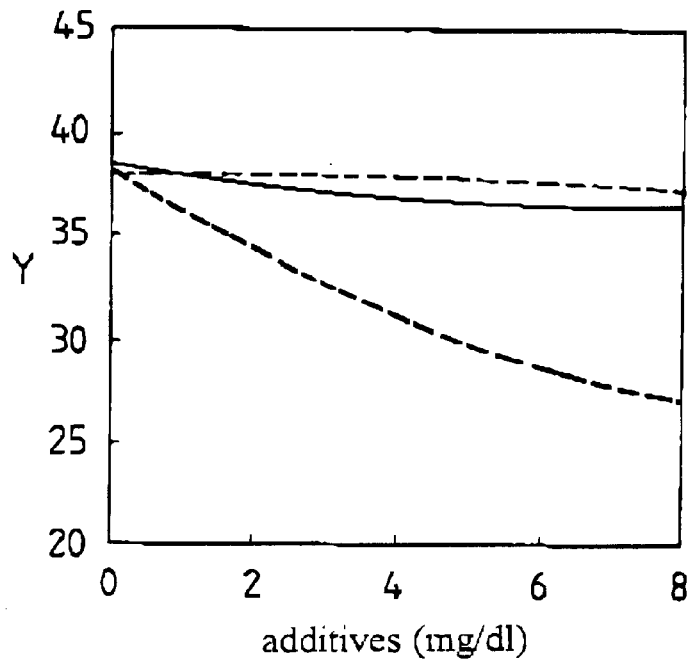
FIG. 9 represents the uric acid determination results using the test strips with an interference-eliminating membrane in the presence of ascorbic acid (AA) and cysteine, wherein the vertical axis represents a reflection value at a wave length of 557 nm, Y value, and the horizontal axis represents the concentration of additives or uric acid. In (a), the lines •••, ——— and — respectively represent the calibration curves of cysteine, uric acid and ascorbic acid. In (b) the lines, ———, — and ••• respectively represent the calibration curves of uric acid containing 0, 2 and 10 mg/dl ascorbic acid. In (c) the lines, ———, — and ••• respectively represent the calibration curves of uric acid containing 0, 15 and 150 mg/dl cysteine.
Figure 9B:
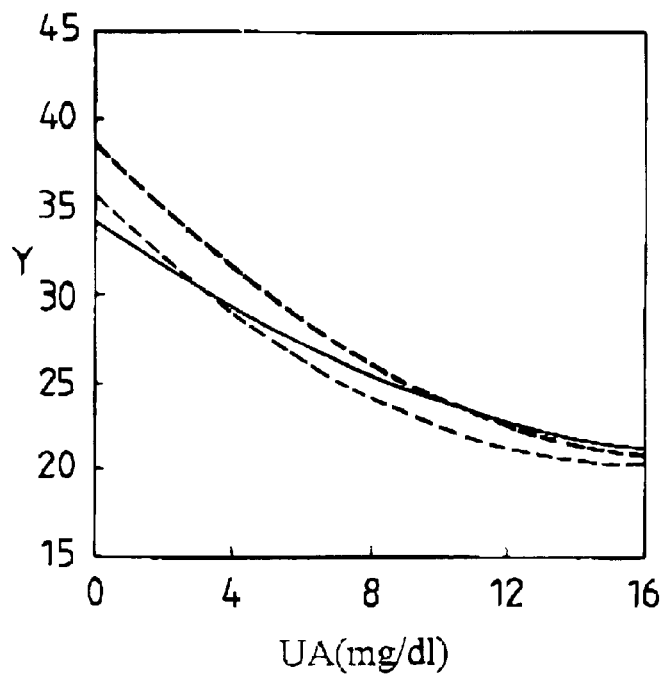
Figure 9C:
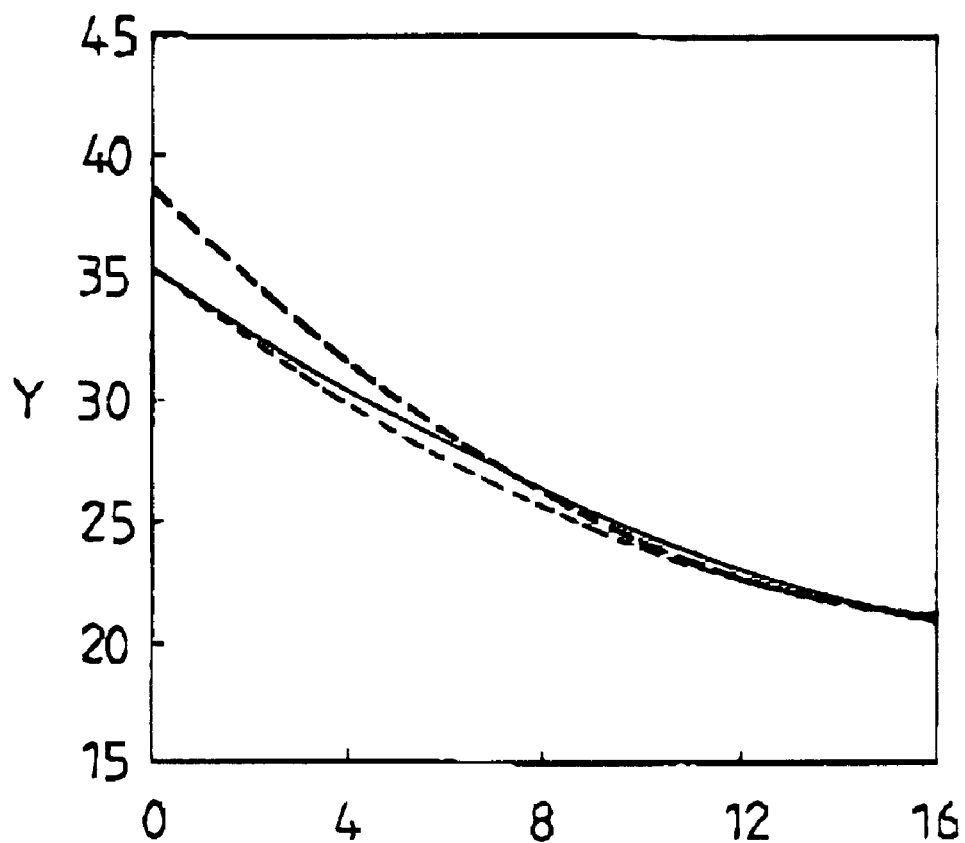

As illustrated in FIGS. 8(A)–8(C), the Y values of ascorbic acid and cysteine was smaller than those of uric acid when a cysteine EIM were not assembled into the test strips. It is clearly showed in FIG. 8(A) that the color change of ascorbic acid was more obvious than that of uric acid. Therefore, the test strip without a cysteine EIM could not specifically detect uric acid in a sample. To the contrary, as illustrated in FIGS. 9(A)—9(C), ascorbic acid and cysteine did not substantially affect the color development of uric acid. It is clearly showed in FIG. 9(A) that the color change due to uric acid was prior to the color development of ascorbic acid and cysteine on the test strip including a cysteine EIM. Therefore, the test results demonstrated that the test strip with cysteine specifically detected uric acid in a sample.

Example 8

The Effects on the $Cu^{2+}$ ion and Bicinchoninate With Potassium Iodate ($KIO_3$)

The test strip consisting of an interference-eliminating membrane (2% of $KIO_3$ in 0.3M $NaHSO_4$), a reaction layer (6 ml of mixture of $Cu^{2-}$, bicinchoninate and citrate) and pH modifying laxer (1.875% NaOH) was similarly prepared based on the previous examples. The test strip was tested by 20 mM PBS (phosphate-buffer-saline), 10 mg/dl uric acid solution and 10 mg/dl ascorbic acid solution, respectively. The results were read after adding the sample for 2.5 hours. The data are as follows:

| Sample | Y value |
| --- | --- |
| 20 mM PBS | 40.00 |
| 10 mg/dl uric acid solution | 32.99 |
| 10 mg/dl ascorbic acid | 39.77 |

As shown in the data, the PBS buffer and ascorbic acid have little change in color. However, uric acid presents the color purple. The results demonstrated that the interference-eliminating membrane of $KIO_3$ can remove the interference due to ascorbic acid in the uric acid assay, The examples provided above are not meant to be exclusive. Many other variations and modifications of the above described embodiments of the present invention would be carried out without departing from the spirit and scope of this invention.

What is claimed is:

1. A test strip for use in detecting uric acid in a sample, comprising one or more reaction layers including test reagents and a carrier, wherein the test reagents are selected from the group consisting of (a) ammonium phosphotungstate at a pH value of 2–5 and a basic material, provided that the phosphotungstate cannot have a substantive reaction with the basic material before the addition of the sample, and (b) a $Cu^{2+}$ ion, bicinchoninate and citrate, provided that the $Cu^{2+}$ ion cannot have a substantive reaction with the bicinchoninate before addition of the sample.

2. The test strip according to claim 1, wherein said basic material is selected from a group consisting of carbonate, glycine, carbonate-ureidoethanolamine or sodium hydroxide.

3. The test strip according to claim 1, wherein the $Cu^{2+}$ ion and bicinchoninate are respectively obtained form copper sulfate and sodium bicinchoninate.

4. The test strip according to claim 1, which is applied in over the counter pharmacies or dispensaries for uric acid detection.

5. A kit for use in detecting uric acid in a sample, comprising the test strip of claim 1.

6. The kit according to claim 5, further comprising a color card, to be compared with the test results, wherein the colors card presents color from almost white to deep blue or violet under the reaction of different uric acid concentration with the reagent.

7. The kit according to claim 6, further comprising a photometer comparing with the test results, wherein the color development has been stored as digital or analog data under the reaction of different uric acid concentration with reagent.

8. A test strip for detecting uric acid in a sample, said test strip comprising (i) a plurality of reagents that, upon contact with uric acid in the sample, undergo a substantive reaction to form a detectable product, said plurality of reagents being selected from the group consisting of (a) ammonium phosphotungstate at a pH value of 2–5 and a basic material, and (b) a $Cu^{2+}$ ion bicinchoninate and citrate;

(ii) reaction layer means, comprising at least one reaction layer, for carrying the plurality of reagents in a manner that allows said reagents to undergo said substantive reaction after and only after the test strip has been contacted with uric acid in the sample; and (iii) interference-eliminating membrane means for inhibiting or shading a substance in the sample that can interfere in the substantive reaction.

9. The test strip according to claim 8, wherein the membrane means comprises a carrier that is disposed in the test strip to allow the sample to be loaded onto the carrier and, after loading, to flow from the carrier to the reaction layer means.

10. The test strip according to claim 9, wherein the substance has a reducing ability that is higher than that of uric acid and the membrane means comprises a compound that selectively oxidizes the substance.

11. The test strip according to claim 10, wherein the compound is selected from the group consisting of an iodate, a ferric salt, $KMnO_4$, $K_2CrO_4$, $Ce(SO_4)_2$, cysteine and glutathion.

12. The test strip according to clam 9, wherein the membrane means comprises a compound that comprises at least one mercapto group.

* * * * *